US008895605B2

(12) United States Patent
Rathos et al.

(10) Patent No.: US 8,895,605 B2
(45) Date of Patent: Nov. 25, 2014

(54) PYRROLIDINE-SUBSTITUTED FLAVONES AS RADIO-SENSITIZERS FOR USE IN THE TREATMENT OF CANCER

(75) Inventors: Maggie Joyce Rathos, Mumbai (IN); Kalpana Sanjay Joshi, Mumbai (IN); Nikhil Krishnamurthy Hebbar, Mumbai (IN); Somesh Sharma, Mumbai (IN)

(73) Assignee: Piramal Enterprises Limited, Mumbai (IN)

( * ) Notice: Subject to any disclaimer, the term of this patent is extended or adjusted under 35 U.S.C. 154(b) by 377 days.

(21) Appl. No.: 13/318,235

(22) PCT Filed: May 3, 2010

(86) PCT No.: PCT/IB2010/051921
§ 371 (c)(1),
(2), (4) Date: Oct. 31, 2011

(87) PCT Pub. No.: WO2010/128443
PCT Pub. Date: Nov. 11, 2010

(65) Prior Publication Data
US 2012/0046334 A1    Feb. 23, 2012

Related U.S. Application Data

(60) Provisional application No. 61/224,524, filed on Jul. 10, 2009.

(30) Foreign Application Priority Data
May 5, 2009  (IN) .......................... 1174/MUM/2009

(51) Int. Cl.
*A61K 31/4025*  (2006.01)
*C07D 311/32*  (2006.01)
*A61P 35/00*  (2006.01)
*A61K 31/00*  (2006.01)

(52) U.S. Cl.
CPC ............. *A61K 31/00* (2013.01); *A61K 31/4025* (2013.01)
USPC ............ 514/422; 514/453; 514/456; 548/525

(58) Field of Classification Search
CPC ......................... A61K 31/4025; C07D 311/22
USPC ............................ 514/422, 453, 456; 548/525
See application file for complete search history.

(56) References Cited

U.S. PATENT DOCUMENTS

| 4,900,727 A | 2/1990 | Kattige et al. |
| 7,272,193 B2 | 9/2007 | Fwu |

FOREIGN PATENT DOCUMENTS

| WO | 00/61187 A1 | 10/2000 |
| WO | 2004/004632 A3 | 7/2003 |
| WO | 2007/148158 A1 | 12/2007 |
| WO | 2008/007169 | 11/2008 |
| WO | 2008/139271 A2 | 11/2008 |

OTHER PUBLICATIONS

Fischer P M et al.: "CDK inhibitors in clinical development for the treatment of cancer" Expert Opinion on Investigational Drugs 20030601 GB LNKD-DOI: 10.1517/EOID.12.6.955. 21792, vol. 12, No. 6, Jun. 1, 2003, pp. 955-970, XP002594685 ISSN : 1354-3784.
Wilson Baker; Molecular Rearrangement of Some o-Acyloxyacetophenones and the Mechanism of the Production of 3-Acylchromones; J. Chem. Soc.; 1933, p. 1381.
K. Venkataraman, et al.; A Synthesis of Flavones at Room Temperature; J. Indian Chem. Soc.; Dec. 1933; pp. 214-215.
Kim Suzy et al.; "Enhancement of radiation effects by flavopiridol in uterine cervix cancer cells." Cancer Research and Treatment: Official Journal of Korean Cancer Association Jun. 2005 LNKD-PUBMED:19956502, vol. 37, No. 3, Jun. 2005, pp. 191-195, XP002594686 ISSN: 2005-9256.
Jung C et al.; "The Cyclin-Dependent Kinase Inhibitor Flavopiridol Potentiates [gamma]-Irradiation-Induced Apoptosis in Colon and Gastric Cancer Cells" Clinical Cancer Research 20031201 US, vol. 9, No. 16 I, Dec. 1, 2003, pp. 6052-6061, XP002594687 ISSN: 1078-0432.
K. Venkataraman, et al.; Synthetical Experiments in the Flavone and Isoflavone groups; (Read at Symposium, Sep. 26-27, 1938.); vol. V-No. 2; Published Jun. 5, 1939; pp. 253-260.
Jae-Chul Kim, et al.; Enhancement of radiation effects by combined docetaxel and flavopiridol treatment in lung cancer cells; Radiotherapy and Oncology 71 (2004) 213-221.
Ting-Chao Chou; Theoretical Basis, Experimental Design, and Computerized Simulation of Synergism and Antagonism in Drug Combination Studies; vol. 58, No. 3; Pharmacol Rev 58: pp. 621-681, 2006.
Zhong Wang, et al.; Synthesis and biologic properties of hydrophilic sapphyrins, a new class of tumor-selective inhibitors of gene expression; Molecular Cancer 2007, 6:9; pp. 1-12.
Lawrence Kleinberg, et al.; Chemoradiotherapy for localized esophageal cancer: regimen selection and molecular mechanisms of radiosensitization; Nature Clinical Practice Oncology May 2007; vol. 4 No. 5; pp. 282-294.
Ek Rofstad, et al.; Hypoxia-induced treatment failure in advanced squamous cell carcinoma of the uterine cervix is primarily due to hypoxia-induced radiation resistance rather than hypoxia-induced metastasis; British Journal of Cancer (2000) 83(3), pp. 354-359.

*Primary Examiner* — Renee Claytor
*Assistant Examiner* — Sahar Javanmard
(74) *Attorney, Agent, or Firm* — Ladas & Parry LLP

(57) ABSTRACT

The present invention relates to a combination for the treatment of cancer wherein the combination exhibits a synergistic effect. The combination comprises radiation and at least one cyclin dependent kinase (CDK) inhibitor selected from the compounds of formula I or a pharmaceutically acceptable salt or a solvate thereof. The present invention also relates to a method for the treatment of cancer, which method comprises administering to a patient in need of such a treatment, a therapeutically effective amount of the combination. The present invention also relates to the use of a CDK inhibitor selected from the compounds of formula I as a radiosensitizer that enhances the efficacy of radiotherapy for the treatment of cancer, particularly head and neck cancer.

6 Claims, 6 Drawing Sheets

Figure 1: Effect of 1 µM of Compound A (48 h treatment) on the radioresponse in FaDu cell line (3500 cells / plate)
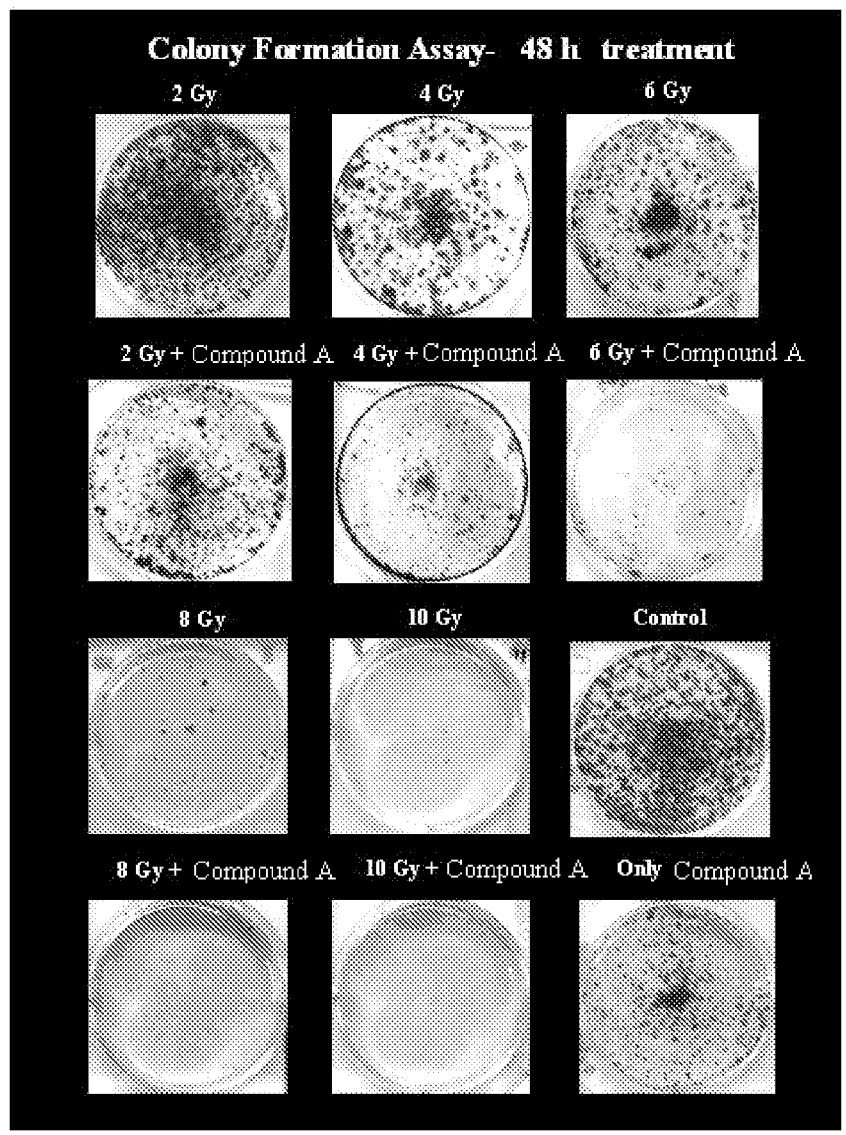

Figure 2: Effect of 1 µM of Compound A (96 h treatment) on the radio response in FaDu cell line (3500 cells / plate)
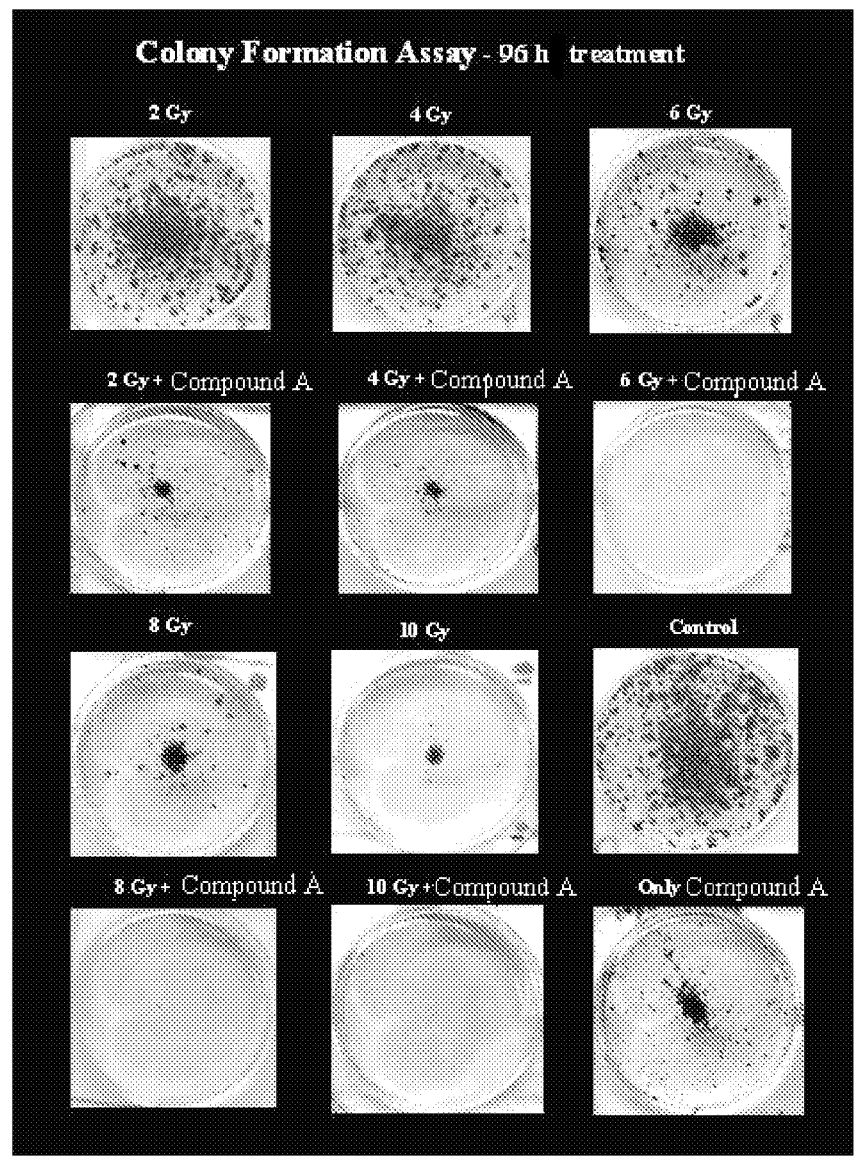

Figure 3: Effect of 1 µM of Compound A (72 h treatment) on the radioresponse in FaDu cell line (1500 cells / plate)
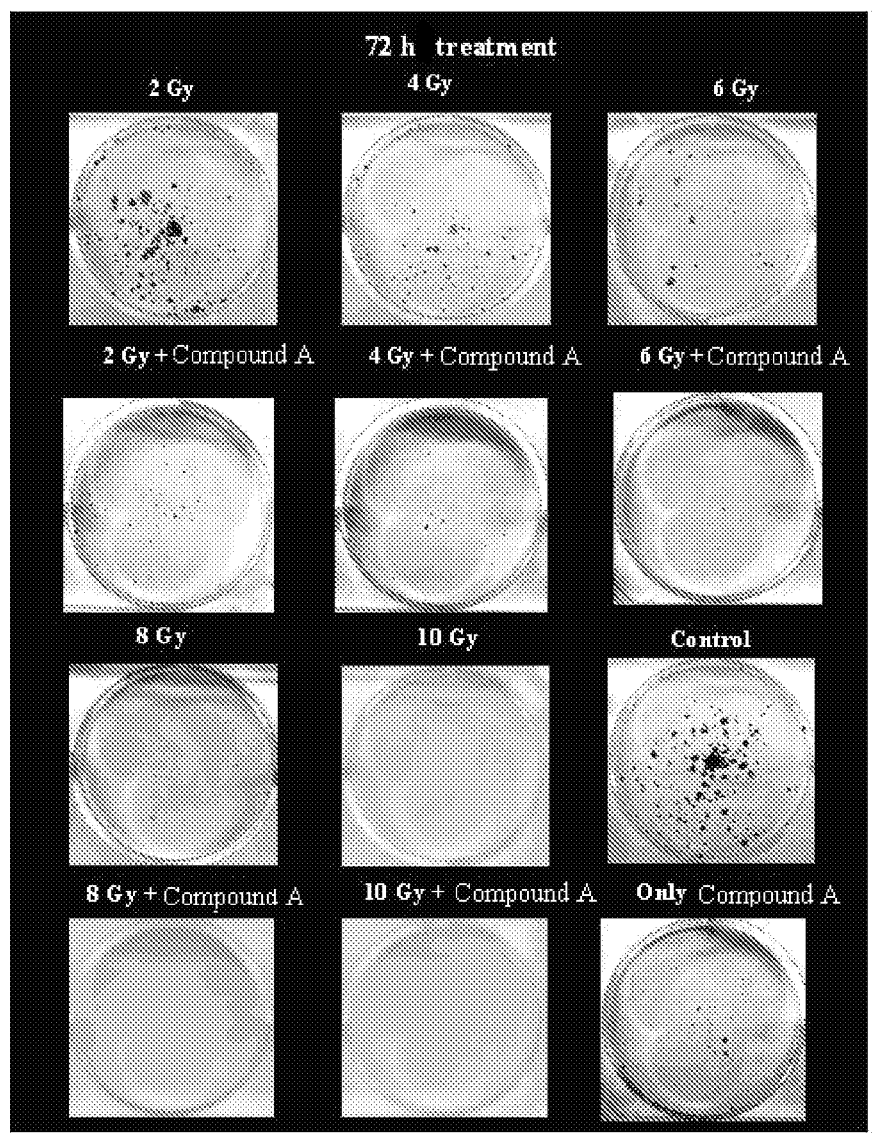

Figure 4 : Effect of 1 µM of Compound A (96 h treatment) on the radioresponse in FaDu cell line (1500 cells / plate)
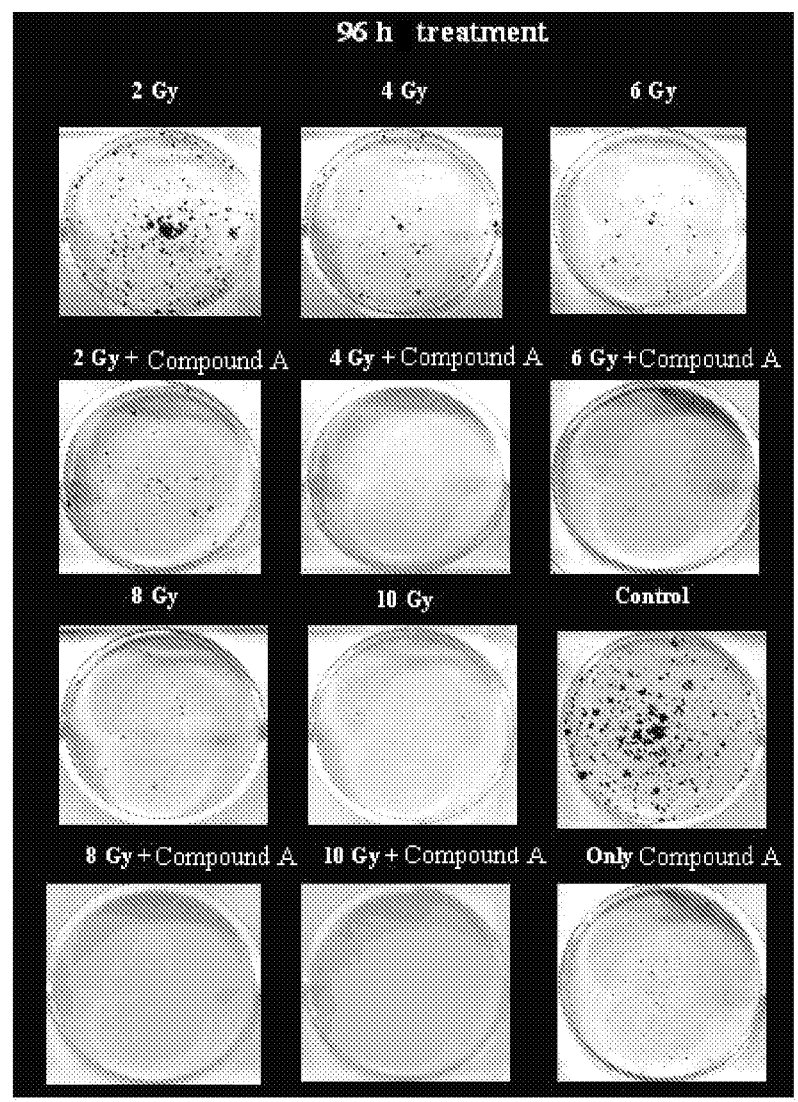

Figure 5: Average group body weight over the period of administration of radiation, Compound A, combination and control.
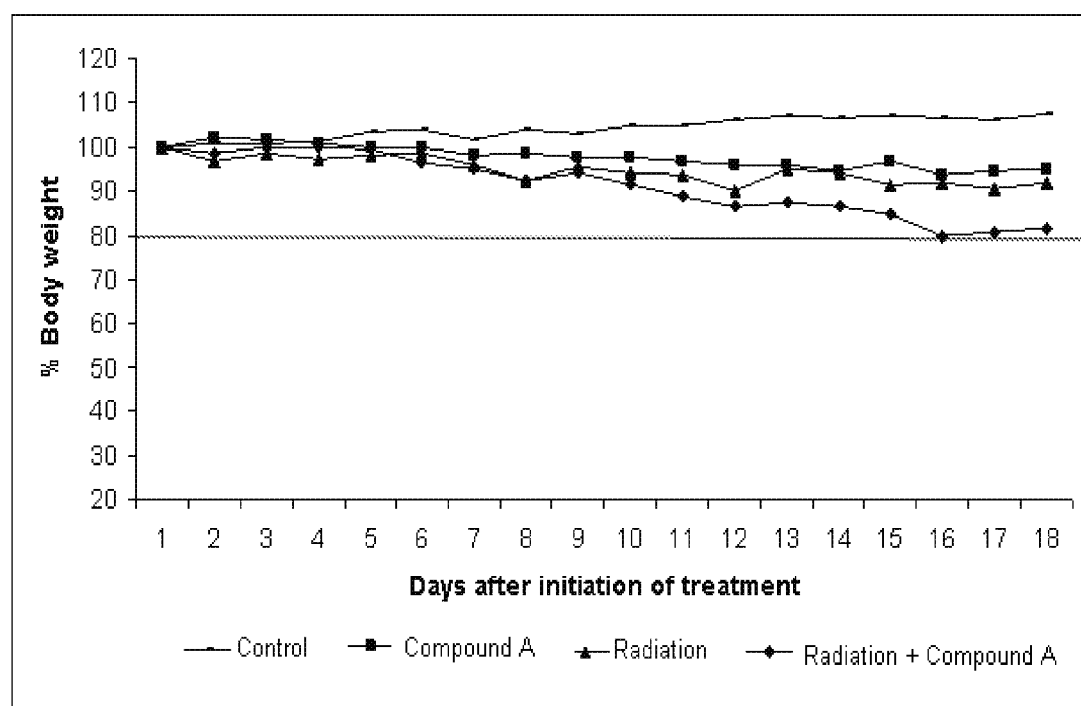

Figure 6: Average % tumor weight of Head and Neck carcinoma (FaDu) xenograft over the period of administration of radiation, Compound A, combination and control.
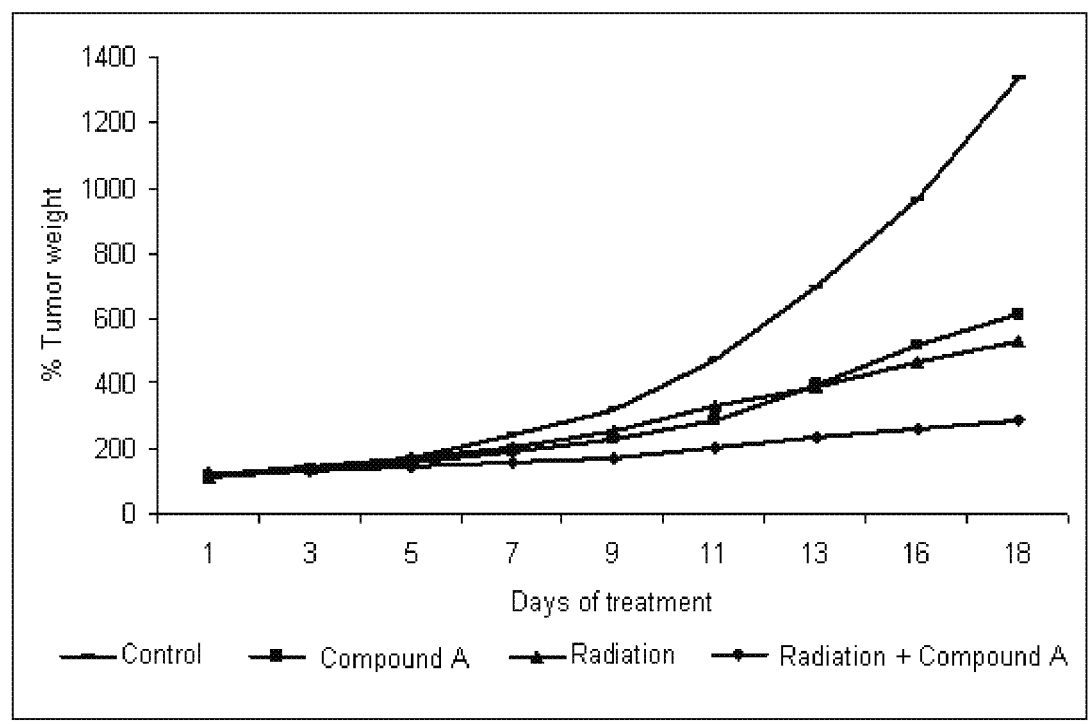

PYRROLIDINE-SUBSTITUTED FLAVONES AS RADIO-SENSITIZERS FOR USE IN THE TREATMENT OF CANCER

CROSS-REFERENCE TO RELATED APPLICATIONS

This application is a 371 of International Application PCT/IB2010/051921 filed 3 May 2010, which claims the benefit of Indian Application No. 1174/MUM/2009 filed 5 May 2009 and U.S. Provisional Application No. 61/224,524 filed 10 Jul. 2009.

FIELD OF THE INVENTION

The present invention relates to a combination for the treatment of cancer wherein the combination exhibits a synergistic effect. The combination comprises radiation and at least one cyclin dependent kinase (CDK) inhibitor selected from the compounds of formula I (as described herein) or a pharmaceutically acceptable salt or a solvate thereof. The present invention also relates to a method for the treatment of cancer, particularly head and neck cancer, which method comprises administering to a patient in need of such a treatment, a therapeutically effective amount of the combination. The present invention also relates to the use of a CDK inhibitor selected from the compounds of formula I as a radiosensitizer that enhances the efficacy of radiotherapy for the treatment of cancer, particularly head and neck cancer.

BACKGROUND OF THE INVENTION

Most radiosensitizing agents that are useful in the treatment of cancer have been identified from empiric laboratory or clinical observations, without adequate knowledge of the molecular basis of interaction of these agents. Efforts to enhance the efficacy of radiation are based on exploitation of the mechanisms of radiation effect and resistance. The six general mechanisms are as follows: hypoxic sensitization, enhancement of DNA injury, decreased DNA repair, increased apoptotic cell death resulting from DNA injury, effects on tumor vasculature, and cell-cycle effects (Nature Clinical Practice Oncology, 2007, 4(5), 282-294). For decades, investigations focused on the problem of tumor hypoxia as a cause of radiation resistance (British Journal of Cancer, 2000, 83(3), 354-359). Hypoxic cells are resistant to radiation in vitro and in vivo. Early experiments indicated that a modest amount of oxygen was required for DNA injury at the moment that radiation was administered; but that once a threshold level of oxygen was present (e.g. as in normal tissues) giving more oxygen would not further enhance the radiation effect. Oxygen is necessary for free-radical-mediated radiation induced DNA injury. It was proposed that resistant hypoxic-cell populations could be a major cause of treatment failure and this could be overcome by enhancing oxygen delivery or administering drugs that act like molecular oxygen. Drugs that preferentially kill hypoxic tumor cells, such as mitomycin and tirapazamine, show potential benefit and are under study.

Despite the importance of the phenomenon of hypoxia, efforts addressing tumor hypoxia have not been successful. Several potential reasons for this failure include toxicity of the agents, which limits dosing, self-correction of hypoxia that occurs during fractionated radiotherapy, whereby the death of normoxic cells allows oxygen to reach formerly hypoxic cells, hypoxia-mediated upregulation of resistance genes, and the fact that the existence of hypoxia is a marker for a resistant tumor rather than the cause of aggressiveness (Nature Clinical Practice Oncology, 2007, 4(5), 282-294).

The limited success at overcoming hypoxia has led to other approaches being developed to enhance radiation efficacy. The most studied and clinically successful approach for combating tumor hypoxia is the administration of cytotoxic chemotherapy concomitantly with radiation. The mechanisms that result in improved outcome with this combination include the following: simple independent additive effects on cell killing; arrest of cells in a radio sensitive portion of the cell cycle (e.g. G2-M); targeting of resistant populations such as hypoxic cells or those in resistant parts of the cell cycle; and enhancing radiation-induced DNA injury or preventing its repair. Additionally, a tumor can proliferate in due course of radiation with a rate of growth that could counteract much of the cytotoxic effect of radiation. This proliferation is termed accelerated repopulation, and can occur as a result of improved nutrients and blood supply to surviving cells or a remaining population of radiation-resistant cells. This proliferative response may be overcome by using a cytotoxic agent in addition to radiation. Chemotherapy has been combined with radiotherapy in an effort to optimize the therapeutic index of radiotherapy in treatment of cancer. It is desirable to develop radiosenstitizers that augment the efficacy of radiation therapy for cancer, thus allowing a lower radiation dose, potential target specificity and clinically acceptable toxicity.

PCT Patent Publication No. WO2004004632 (corresponding to U.S. Pat. No. 7,272,193) and PCT Patent Publication No. WO2007148158 describe pyrrolidine substituted flavones as CDK inhibitors with utility in the treatment of different types of cancers. CDK inhibitors are less toxic and hence it would be advantageous to evaluate the effect and possible mechanism of CDK inhibitors on enhancing the radiosensitivity in human cancer. This would be highly beneficial to cancer treatment through radiation.

SUMMARY OF THE INVENTION

In one aspect, the present invention relates to a combination comprising radiation and a cyclin dependent kinase (CDK) inhibitor selected from the compounds of formula I (as described herein) or a pharmaceutically acceptable salt or a solvate thereof; wherein the combination exhibits synergistic effect in the treatment of cancer.

In another aspect, the present invention relates to a combination comprising radiation and a cyclin dependent kinase (CDK) inhibitor selected from the compounds of formula I or a pharmaceutically acceptable salt or a solvate thereof, for simultaneous or sequential administration for the treatment of cancer.

In a further aspect, the present invention relates to use of the combination comprising radiation and a cyclin dependent kinase (CDK) inhibitor selected from the compounds of formula I or a pharmaceutically acceptable salt or a solvate thereof, for the treatment of cancer.

In another aspect, the present invention relates to a method of treating cancer, which method comprises administering to a subject in need thereof a therapeutically effective amount of radiation in combination with a therapeutically effective amount of a cyclin dependent kinase (CDK) inhibitor selected from the compounds of formula I or a pharmaceutically acceptable salt or a solvate thereof.

In a still further aspect, the present invention relates to the use of a CDK inhibitor selected from the compounds of formula I as a radiosensitizer that enhances the efficacy of radiotherapy for the treatment of cancer.

Other aspects and further scope of applicability of the present invention will become apparent from the detailed description to follow.

BRIEF DESCRIPTION OF THE DRAWINGS

FIG. 1 depicts the effect of 1 µM of Compound A (48 h treatment) on the radioresponse in FaDu cell line (3500 cells/plate).

FIG. 2 depicts the effect of 1 µM of Compound A (96 h treatment) on the radioresponse in FaDu cell line (3500 cells/plate).

FIG. 3 depicts the effect of 1 µM of Compound A (72 h treatment) on the radioresponse in FaDu cell line (1500 cells/plate).

FIG. 4 depicts the effect of 1 µM of Compound A (96 h treatment) on the radioresponse in FaDu cell line (1500 cells/plate).

FIG. 5 depicts the average group body weight over the period of administration of radiation, Compound A, combination and control.

FIG. 6 depicts the average % tumor weight of Head and Neck carcinoma (FaDu) xenograft over the period of administration of radiation, Compound A, combination and control.

DETAILED DESCRIPTION OF THE INVENTION

The present invention relates to a combination, which comprises radiation and a CDK inhibitor selected from the compounds of formula I (as described herein) or a pharmaceutically acceptable salt or a solvate thereof, that exhibits synergistic effect when used in the treatment of cancer, particularly head and neck cancer.

The CDK inhibitors represented by the following formula I are disclosed in PCT Patent Publication No WO2004004632 (corresponding to U.S. Pat. No. 7,272,193) and PCT Patent Publication No WO2007148158, which are incorporated herein by reference. The compounds of formula I are CDK inhibitors, which inhibit proliferation of many cancer cells. The compounds of formula I as used in the present invention are effective against various solid and hematological malignancies. The inventors of the present invention observed that combining CDK inhibitors of formula I with radiation resulted in an increase in apoptosis, or programmed cell death.

The general terms used hereinbefore and hereinafter preferably have a meaning within the context of this disclosure the following meanings, unless otherwise indicated:

The singular forms "a," "an," and "the" include plural reference unless the context clearly dictates otherwise.

As used herein, the term "synergistic" means that the effect achieved with the methods and combinations of this invention is greater than the sum of the effects that result from using radiation, and CDK inhibitor of formula I or a pharmaceutically acceptable salt or a solvate thereof, separately under the same dosage conditions. Advantageously, such synergy provides greater efficacy at the same doses, and/or prevents or delays the build-up of multi-drug resistance.

As used herein the term "therapeutically effective amount" refers to an amount of radiation or CDK inhibitor of formula I, which provides the maximum apoptosis of proliferative cells at the least toxicity to nonproliferative cells.

As used herein, the term "therapeutic synergy" represents a therapeutic effect achieved with a tolerated regimen of a combination treatment of radiation and CDK inhibitor of formula I, that exceeds the optimal effect achieved at any tolerated dose of monotherapy using radiation or the CDK inhibitor alone.

The term "apoptosis" refers to a type of cell death in which a series of molecular steps in a cell leads to its death. This is the body's normal way of getting rid of unneeded or abnormal cells. The process of apoptosis may be blocked in cancer cells. Apoptosis is also referred to as programmed cell death. As used herein the term "increasing apoptosis" is defined as an increase in the rate of programmed cell death, i.e. more cells are induced into the death process as compared to exposure (contact) with either radiation alone or the CDK inhibitor alone.

The term "subject" as used herein, refers to an animal, preferably a mammal, most preferably a human, who has been the object of treatment, observation or experiment.

Head and neck cancer refers to a group of biologically similar cancers originating from the upper aero digestive tract, including the lip, oral cavity, nasal cavity, paranasal sinuses, pharynx, and larynx. Head and neck squamous cell carcinomas (HNSCC's) make up the vast majority of head and neck cancers, and arise from mucosal surfaces throughout this anatomic region. These include tumors of the nasal cavities, paranasal sinuses, oral cavity, nasopharynx, oropharynx, hypopharynx, and larynx.

Cancers of the head and neck are identified by the area in which they begin:

1. Oral cavity: Squamous cell cancers are common in the oral cavity, including the inner lip, tongue, floor of mouth, gingivae, and hard palate.
2. Nasopharynx: Nasopharyngeal cancer arises in the nasopharynx, the region in which the nasal cavities and the Eustachian tubes connect with the upper part of the throat.
3. Oropharynx: Oropharyngeal cancer begins in the oropharynx, the middle part of the throat that includes the soft palate, the base of the tongue, and the tonsils. Squamous cell cancers of the tonsils are more strongly associated with human papillomavirus infection than are cancers of other region of head and neck.
4. Hypopharynx: The hypopharynx includes the pyriform sinuses, the posterior pharyngeal wall, and the postcricoid area. Tumors of the hypopharynx frequently have an advanced stage at diagnosis, and have the most adverse prognoses of pharyngeal tumors. They tend to metastasize early due to extensive lymphatic network around the larynx.
5. Larynx: Laryngeal cancer begins in the larynx. Cancer may occur on the vocal folds themselves ("glottic" cancer), or on tissues above and below the true cords ("supraglottic" and "subglottic" cancers respectively).
6. Trachea: Cancer of the trachea is a rare malignancy which can be biologically similar in many ways to head and neck cancer, and is sometimes classified as such.

The mode of treatment of patients with HNSCC's depends on the site and stage of the disease and on overall health status of the patient. Surgical resection and radiation therapy are the mainstays of treatment for most head and neck cancers and remain the standard of care in most cases. Because of unsatisfactory results obtained in patients with unresectable and/or inoperable locally advanced head and neck cancers who are only treated with radiotherapy, concurrent chemotherapy-radiation therapy is being investigated.

The CDK inhibitors used in the present invention are selected from the compounds represented by the following formula I,

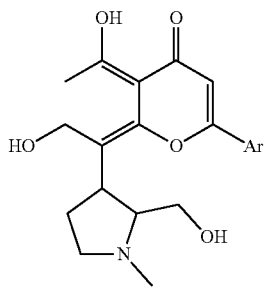

Formula I wherein Ar is a phenyl group, which is unsubstituted or substituted by 1, 2, or 3 identical or different substituents selected from: halogen such as chloro, bromo, fluoro or iodo; nitro, cyano, $C_1$-$C_4$-alkyl, trifluoromethyl, hydroxy, $C_1$-$C_4$-alkoxy, carboxy, $C_1$-$C_4$-alkoxycarbonyl, $CONH_2$, and $NR_1R_2$;

wherein $R_1$ and $R_2$ are each independently selected from hydrogen or $C_1$-$C_4$-alkyl.

In an embodiment, the CDK inhibitor is the (+)-trans isomer of the compound of formula I, as indicated in Formula IA below,

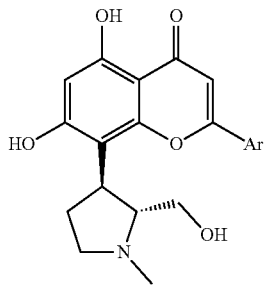

Formula IA wherein Ar is a phenyl group, which is unsubstituted or substituted by 1, 2, or 3 identical or different substituents selected from: halogen such as chloro, bromo, fluoro or iodo; nitro, cyano, $C_1$-$C_4$-alkyl, trifluoromethyl, hydroxy, $C_1$-$C_4$-alkoxy, carboxy, $C_1$-$C_4$-alkoxycarbonyl, $CONH_2$, and $NR_1R_2$;

wherein $R_1$ and $R_2$ are each independently selected from hydrogen or $C_1$-$C_4$-alkyl.

The compounds of formula I may be prepared according to the methods disclosed in PCT Patent Publication No. WO2004004632 and PCT Patent Publication No. WO2007148158, which are incorporated herein by reference. The method described in the following Scheme I can be used to prepare intermediate of formula (VIA).

SCHEME 1

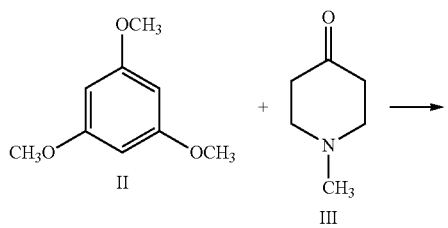

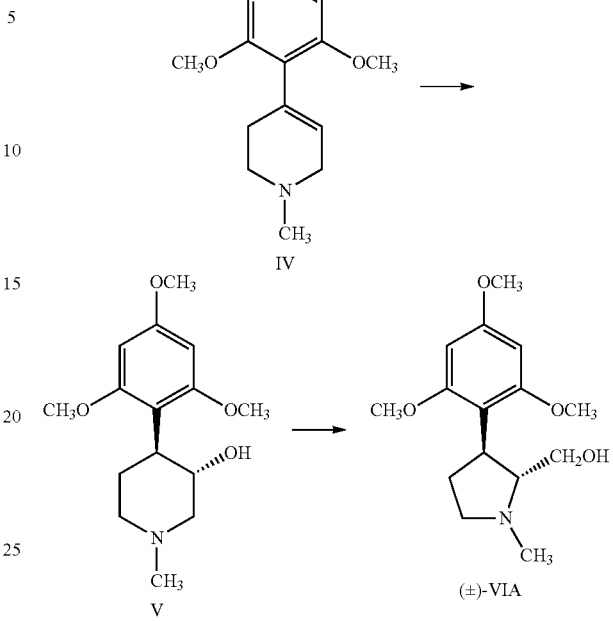

The preparation steps up to the compound of formula V starting from the compound of formula (II) are described in U.S. Pat. No. 4,900,727, which is incorporated herein by reference. 1-Methyl-4-piperidone (compound of formula III) is reacted with a solution of 1,3,5-trimethoxybenzene (compound of formula II) in glacial acetic acid, to yield 1-methyl-4-(2,4,6-trimethoxyphenyl)-1,2,3,6-tetrahydropyridine (compound of formula IV). Compound of formula IV is reacted with boron trifluoride diethyl etherate, sodium borohydride and tetrahydrofuran to obtain compound of formula V. In the conversion of the compound of formula V to that of formula VIA in the above scheme, the hydroxyl function on the piperidine ring may be converted to a leaving group such as tosyl, mesyl, triflate or halide by treatment with an appropriate reagent such as p-toluenesulfonylchloride, methanesulfonylchloride, triflic anhydride or phosphorous pentachloride in the presence of oxygen nucleophiles such as triethylamine, pyridine, potassium carbonate or sodium carbonate, followed by ring contraction in the presence of oxygen nucleophiles such as sodium acetate or potassium acetate in an alcoholic solvent such as isopropanol, ethanol or propanol. The ring contraction involved in this step may be effected before flavone formation as depicted in the above scheme or it may be done after building the flavone with the desired substitutions.

Enantiomerically pure (−)-trans enantiomer of an intermediate compound of the formula VIA as defined, is used for the preparation of an enantiomerically pure compound of the formula I. By using an intermediate having a high enantiomeric purity as a starting compound in the process, the resultant (+)-trans enantiomer of pyrrolidines substituted with flavone represented by formula I produced by the process has a correspondingly high enantiomeric purity.

The process for the preparation of an enantiomerically pure (+)-trans enantiomer of a compound of formula I, or a pharmaceutically acceptable salt thereof, from the resolved enantiomerically pure (−)-trans enantiomer of the intermediate compound of formula VIA comprises the following steps:

(a) treating the resolved enantiomerically pure (−)-trans enantiomer of the intermediate compound of formula VIA,

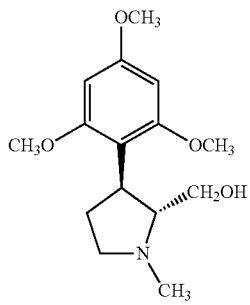

VIA with acetic anhydride in the presence of a Lewis acid catalyst to obtain a resolved acetylated compound of formula VIIA,

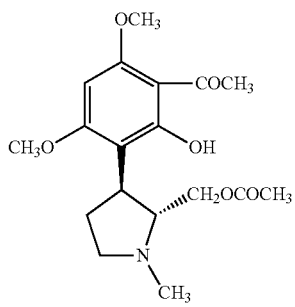

VIIA (b) reacting the resolved acetylated compound of formula VIIA with an acid of formula ArCOOH or an acid chloride of formula ArCOCl or an acid anhydride of formula (ArCO)$_2$O or an ester of formula ArCOOCH$_3$, wherein Ar is as defined hereinabove, in the presence of a base and a solvent to obtain a resolved compound of formula VIIIA;

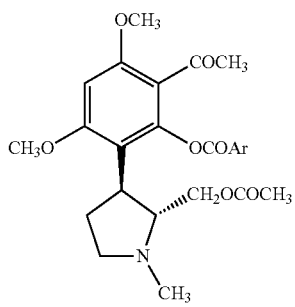

VIIIA (c) treating the resolved compound of formula VIIIA with a base in a suitable solvent to obtain the corresponding resolved β-diketone compound of formula IXA;

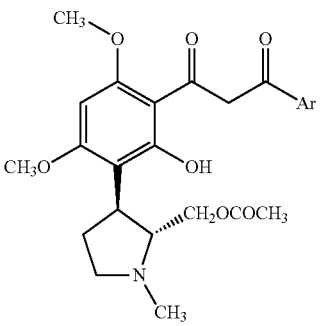

IXA where Ar is as defined above.

(d) treating the resolved β-diketone compound of formula IXA with an acid such as hydrochloric acid to obtain the corresponding cyclized compound of formula XA,

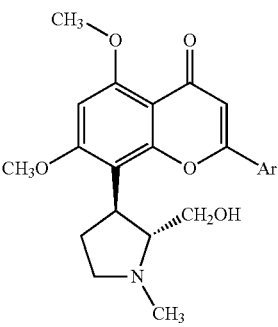

XA (e) subjecting the compound of formula XA to dealkylation by heating it with a dealkylating agent at a temperature ranging from 120-180° C. to obtain the (+)-trans enantiomer of the compound of formula I and, optionally, converting the subject compound into its pharmaceutically acceptable salt.

The Lewis acid catalyst utilized in the step (a) above may be selected from: BF$_3$, Et$_2$O, zinc chloride, aluminium chloride and titanium chloride.

The base utilized in the process step (b) may be selected from triethylamine, pyridine and a DCC-DMAP combination (combination of N,N'-dicyclohexyl carbodiimide and 4-dimethylaminopyridine).

It will be apparent to those skilled in the art, the rearrangement of the compound of formula VIIIA to the corresponding β-diketone compound of formula IXA is known as a Baker-Venkataraman rearrangement (J. Chem. Soc., 1381 (1933) and Curr. Sci., 4, 214 (1933)).

The base used in the process step (c) may be selected from: lithium hexamethyl disilazide, sodium hexamethyldisilazide, potassium hexamethyldisilazide, sodium hydride and potassium hydride. A preferred base is lithium hexamethyl disilazide.

The dealkylating agent used in process step (e) for the dealkylation of the compound of formula IXA may be selected from: pyridine hydrochloride, boron tribromide, boron trifluoride etherate and aluminium trichloride. A preferred dealkylating agent is pyridine hydrochloride.

In an embodiment the CDK inhibitor is a compound of formula I wherein the phenyl group is substituted by 1, 2, or 3 identical or different substituents selected from: halogen selected from chlorine, bromine, fluorine or iodine, $C_1$-$C_4$-alkyl or trifluoromethyl.

In another embodiment the CDK inhibitor is a compound of formula I wherein the phenyl group is substituted by 1, 2, or 3 halogens selected from chlorine, bromine, fluorine or iodine.

In another embodiment the CDK inhibitor is a compound of formula I wherein the phenyl group is substituted by chlorine.

The manufacture of the compounds of formula I, which may be in the form of pharmaceutically acceptable salts and solvates, and the manufacture of oral and/or parenteral pharmaceutical composition containing the above compounds are disclosed in PCT Patent Publication No. WO2004004632 and PCT Patent Publication No. WO2007148158. These PCT Patent Publications disclose that the CDK inhibitors represented by formula I inhibit proliferation of many cancer cells. As indicated herein above the CDK inhibitors of formula I may be used in the form of their salts or solvates. Preferred salt of compounds of formula I include hydrochloride salt, methanesulfonic acid salt and trifluoroacetic acid salt.

The compounds of formula I contain at least two chiral centers and hence exist in the form of two different optical isomers (i.e. (+) or (−) enantiomers). All such enantiomers and mixtures thereof including racemic mixtures are included within the scope of the invention. The enantiomers of the compound of formula I can be obtained as described above, by methods disclosed in PCT Patent Publication No. WO2004004632, WO2008007169 and WO2007148158 or the enantiomers of the compound of formula I can also be obtained by methods well known in the art, such as chiral HPLC and enzymatic resolution. Alternatively, the enantiomers of the compounds of formula I can be synthesized by using optically active starting materials. Thus, the definition of the CDK inhibitor of formula I is inclusive of all possible stereoisomers and their mixtures. The formula I definition includes the racemic forms and the isolated optical isomers having the specified activity.

The radiation used in the combination of the present invention is γ-irradiation. In an embodiment, the source used for γ-irradiation is Cobalt-60, iridium-192, or caesium-137. In a preferred embodiment, the source used for γ-irradiation is Cobalt 60.

In an embodiment, the admissible dose-range of γ-irradiation is 1 to 25 Gray (Gy), per day.

In one embodiment, the combination comprises radiation and a CDK inhibitor, wherein said CDK inhibitor is represented by formula I, or a pharmaceutically acceptable salt or solvate thereof.

In another embodiment, the combination comprises radiation and a CDK inhibitor, wherein said CDK inhibitor is the (+)-trans isomer of the compound of formula I as represented by Formula IA, or a pharmaceutically acceptable salt or solvate thereof.

In yet another embodiment, the combination comprises radiation and a CDK inhibitor, wherein said CDK inhibitor is (+)-trans-2-(2-Chloro-phenyl)-5,7-dihydroxy-8-(2-hydroxymethyl-1-methyl-pyrrolidin-3-yl)-chromen-4-one, or a pharmaceutically acceptable salt thereof.

In one embodiment, the combination comprising radiation and the CDK inhibitor of formula I encompasses those which permit a separate administration, which can be simultaneous, sequential or spaced out over a period of time so as to obtain maximum efficacy of the combination.

For the purpose of the present invention, the CDK inhibitor selected from the compounds of formula I may be administered, for example, prior to, after or concurrent with radiation. In a preferred embodiment of the present invention, radiation is administered prior to administration of the CDK inhibitor of formula I or a pharmaceutically acceptable salt or a solvate thereof, in the dosage range described below. However, the optimum method and sequence for administration of radiation and the CDK inhibitor under given conditions may be suitably selected by those skilled in the art by following routine techniques and the information contained in the present specification.

In one embodiment, the CDK inhibitors of formula I may be administered either orally or parenterally to generate and maintain optimum blood levels thereof.

For oral use, the CDK inhibitors of formula I may be administered, for example, in the form of tablets or capsules, powders, dispersible granules, or cachets, or as aqueous solutions or suspensions. In the case of tablets for oral use, carriers which are commonly used include lactose, corn starch, magnesium carbonate, talc, and sugar, and lubricating agents such as magnesium stearate are commonly added. For oral administration in capsule form, useful carriers include lactose, corn starch, magnesium carbonate, talc and sugar.

For intramuscular, intraperitoneal, subcutaneous and intravenous use, sterile solutions of the CDK inhibitor are usually employed, and the pH of the solutions should be suitably adjusted and buffered.

In one embodiment, the combination of the present invention is used in the treatment of cancer selected from the group comprising head and neck cancer, cervical cancer, breast cancer, lung cancer (including small and non-small cell lung cancer and lung adenocarcinoma), ovarian cancer, pancreatic cancer (including exocrine pancreatic carcinoma), gastric cancer, colorectal cancer, hepatocellular carcinoma, multiple myeloma, mantle cell lymphoma and malignant melanoma.

In a preferred embodiment, the combination of the present invention is used in the treatment of head and neck cancer.

In an embodiment, the combination of the present invention exhibits therapeutic synergy.

In another embodiment, the present invention relates to a method for the treatment of cancer, which method comprises administering to a subject in need of such a treatment a therapeutically effective amount of the combination. Accordingly, in the method of the present invention, cancer is treated in a subject by administering to the subject a therapeutic amount of radiation effective to treat the cancer, in combination with a therapeutically effective amount of a CDK inhibitor selected from the compounds of formula I or a pharmaceutically acceptable salt or a solvate thereof, wherein a synergistic effect results.

In an embodiment, the present invention relates to a method for the treatment of cancer, which method comprises administering to a subject in need of such a treatment, a therapeutic amount of radiation effective to treat the cancer, in combination with a therapeutically effective amount of a CDK inhibitor selected from (+)-trans isomer of the compounds of formula I (as represented by formula IA) or a pharmaceutically acceptable salt or a solvate thereof, wherein a synergistic effect results.

In another embodiment, the present invention relates to a method for the treatment of cancer, which method comprises administering to a subject in need of such a treatment, a therapeutic amount of radiation effective to treat the cancer, in combination with a therapeutically effective amount of a CDK inhibitor, wherein said CDK inhibitor is (+)-trans-2-(2-Chloro-phenyl)-5,7-dihydroxy-8-(2-hydroxymethyl-1-methyl-pyrrolidin-3-yl)-chromen-4-one, or a pharmaceutically acceptable salt thereof.

In an embodiment, the present invention provides a method of treatment of head and neck cancer, cervical cancer, breast cancer, lung cancer, ovarian cancer, pancreatic cancer, gastric cancer, colorectal cancer, hepatocellular carcinoma, multiple myeloma, mantle cell lymphoma and malignant melanoma, which method comprises administering to a subject in need of such a treatment, a therapeutic amount of radiation effective to treat the cancer, in combination with a therapeutically effective amount of the CDK inhibitor.

In another embodiment, the present invention provides a method of treatment of head and neck cancer, which method comprises administering to a subject in need of such a treatment, a therapeutic amount of radiation effective to treat the cancer, in combination with a therapeutically effective amount of the CDK inhibitor.

As indicated herein before, radiation and the CDK inhibitor can be administered simultaneously or sequentially.

In one embodiment, the method of treatment of cancer comprises administering to a subject in need of such treatment a therapeutic amount of radiation simultaneously with a therapeutic amount of the CDK inhibitor.

In another embodiment, the method of treatment of cancer involves sequential administration of a therapeutic amount of radiation and a therapeutic amount of the CDK inhibitor, to a subject in need of such treatment.

In another embodiment, the method of treatment of cancer involves administration to a subject in need of such treatment a therapeutic amount of radiation prior to administration of the CDK inhibitor.

In one embodiment, the present invention relates to use of a CDK inhibitor represented by compounds of formula I or a pharmaceutically acceptable salt or solvate thereof as a radiosensitizer that enhances the efficacy of radiotherapy for the treatment of head and neck cancer, cervical cancer, breast cancer, lung cancer, ovarian cancer, pancreatic cancer, gastric cancer, colorectal cancer, hepatocellular carcinoma, multiple myeloma, mantle cell lymphoma and malignant melanoma.

In another embodiment, the present invention relates to use of a CDK inhibitor selected from (+)-trans isomer of the compounds of formula I or a pharmaceutically acceptable salt or solvate thereof as a radiosensitizer that enhances the efficacy of radiotherapy for the treatment of head and neck cancer, cervical cancer, breast cancer, lung cancer, ovarian cancer, pancreatic cancer, gastric cancer, colorectal cancer, hepatocellular carcinoma, multiple myeloma, mantle cell lymphoma and malignant melanoma.

In another embodiment, the present invention relates to use of a CDK inhibitor as a radiosensitizer that enhances the efficacy of radiotherapy for the treatment of head and neck cancer, cervical cancer, breast cancer, lung cancer, ovarian cancer, pancreatic cancer, gastric cancer, colorectal cancer, hepatocellular carcinoma, multiple myeloma, mantle cell lymphoma and malignant melanoma, wherein said CDK inhibitor is (+)-trans-2-(2-Chloro-phenyl)-5,7-dihydroxy-8-(2-hydroxymethyl-1-methyl-pyrrolidin-3-yl)-chromen-4-one, or a pharmaceutically acceptable salt thereof.

In yet another embodiment, the present invention relates to use of the CDK inhibitor of formula I as a radiosensitizer that enhances the efficacy of radiotherapy for the treatment of head and neck cancer.

In one embodiment, the present invention relates to use of the CDK inhibitor of formula I for preparing an agent (or medicament) for enhancing the efficacy of radiotherapy for the treatment of head and neck cancer, cervical cancer, breast cancer, lung cancer, ovarian cancer, pancreatic cancer, gastric cancer, colorectal cancer, hepatocellular carcinoma, multiple myeloma, mantle cell lymphoma and malignant melanoma.

In a preferred embodiment, the present invention relates to use of said CDK inhibitor of formula I for preparing an agent (or medicament) for enhancing the efficacy of radiotherapy for the treatment of head and neck cancer.

In one embodiment, the combination of the present invention is a medicine for treating head and neck cancer, cervical cancer, breast cancer, lung cancer, ovarian cancer, pancreatic cancer, gastric cancer, colorectal cancer, hepatocellular carcinoma, multiple myeloma, mantle cell lymphoma and malignant melanoma, comprising said CDK inhibitor used with radiotherapy.

In a preferred embodiment, the combination of the present invention is a medicine for treating head and neck cancer comprising the CDK inhibitor of formula I used with radiotherapy.

The actual dosage of the active ingredients contained in the combination may be varied depending upon the requirements of the patient and the severity of the condition being treated. Determination of the proper dosage for a particular situation is within the skill of the art. Generally, treatment is initiated with smaller doses, which are less than the optimum dose of the compound. Thereafter, the dose of each ingredient is increased by small amounts until the optimum effect under the circumstances is reached. However, the amount of each ingredient in the combination will typically be less than an amount that would produce a therapeutic effect if administered alone. In a preferred embodiment, the γ-irradiation and CDK inhibitor represented by the compounds of formula I or a pharmaceutically acceptable salt or a solvate thereof are administered sequentially, such that the γ-irradiation is administered in a synergistically effective dose ranging from 1 to 25 Gy/day, preferably 1 to 10 Gy/day, and the CDK inhibitor is administered in a synergistically effective dose ranging from 5 mg to 750 mg, preferably ranging from 100 mg to 500 mg.

The selected dosage level of γ-irradiation or the CDK inhibitor of formula I will depend upon a variety of factors including the activity of the CDK inhibitor employed and its route of administration, the time of administration, the rate of excretion of the CDK inhibitor employed, the duration of the treatment, other drugs, compounds and/or materials used in combination with the CDK inhibitor employed, the type and stage of cancer being treated, age, sex, weight, condition, general health and prior medical history of the patient being treated, and like factors well known in the medical arts.

The combinations provided by this invention have been evaluated in certain assay systems, and in several different administrative schedules in vitro. The experimental details are as provided herein below. The data presented herein clearly indicate that radiation when combined with a CDK inhibitor of formula I exhibits synergistic effect. It can be clearly observed from the data provided in the tables 1-4 that the CDK inhibitor, a representative compound of formula I designated herein as the Compound A, synergistically enhanced the cytotoxicity of radiation in an in vitro analysis against head and neck cancer cells.

The representative compound, the Compound A used in the pharmacological assays refers to (+)-trans-2-(2-Chloro-phenyl)-5,7-dihydroxy-8-(2-hydroxymethyl-1-methyl-pyrrolidin-3-yl)-chromen-4-one hydrochloride and was one of the compounds disclosed in the published PCT patent applications, WO2004004632 and WO2007148158, which are incorporated herein by reference. The synergistic effect of the combination of the present invention comprising γ-irradiation and a CDK inhibitor is now explained in more details with reference to preferred embodiments thereof. It is to be noted that these are provided only as examples and not intended to limit the invention. Examples 1 to 10 provide the synthesis of Compound A (compound of example 10) while example 11 and 12 provides the combination studies of Compound A in-vitro with radiotherapy. Example 13 provides the in-vivo protocol while example 14 provides the clinical protocol.

The following abbreviations or terms are used herein:
ATCC: American Type Culture Collection
$BF_3$: boron trifluoride
$CHCl_3$: chloroform
$CO_2$: carbon dioxide
DBTA: dibenzoyl tartaric acid
DMSO: dimethylsulfoxide
EtOAc: ethyl acetate
Gy: Gray
HCl: hydrochloric acid
IPA: isopropyl alcohol
KBr: potassium bromide
MeOH: methanol
MTT: 3-(4,5-Dimethylthiazol-2-yl)-2,5-diphenyltetrazolium bromide
$Na_2CO_3$: sodium carbonate
$Na_2SO_4$: sodium sulfate
$NaBH_4$: sodium borohydride
NaOH: sodium hydroxide
TFA: trifluoroacetic acid
THF: tetrahydrofuran

EXAMPLES

Example 1

Preparation of 1-Methyl-4-(2,4,6-trimethoxyphenyl)-1,2,3,6-tetrahydro pyridine 1-methyl-4-piperidone (340 g, 3.0 mol) was added slowly, to a solution of 1,3,5-trimethoxybenzene (500 g, 2.97 mol) in glacial acetic acid (600 mL), maintaining the temperature of the reaction mixture below 40° C. Conc. HCl (450 mL) was added over 20 min. The temperature was raised to 85-90° C. and the reaction mixture was stirred for 3.5 h. It was allowed to cool to 40° C., poured over crushed ice (4 kg) and stirred for 20 min. The precipitate of unreacted 1,3,5-trimethoxybenzene was filtered off. The filtrate was basified, below 10° C., to pH 11-12 using a 50% aqueous NaOH solution. The off white solid obtained was filtered, washed with water and dried to obtain the compound, 1-methyl-4-(2,4,6-trimethoxyphenyl)-1,2,3,6-tetrahydropyridine.

Yield: 580 g (74%); mp: 112-114° C.; IR (KBr): 3045, 2900, 2837, 1600, 1585 $cm^{-1}$; $^1H$ NMR ($CDCl_3$, 300 MHz): δ 6.15 (s, 2H), 5.55 (s, 1H), 3.85 (s, 3H), 3.75 (s, 6H), 3.10 (d, 2H), 2.55 (t, 2H), 2.40 (s, 3H), 2.35 (m, 2H); MS (EI): m/z 263 ($M^+$).

Example 2

Preparation of (±)-trans-1-Methyl-4-(2,4,6-trimethoxyphenyl)-piperidin-3-ol

Boron trifluoride diethyl etherate (300 mL, 2.36 mol) was added slowly with stirring, under an atmosphere of nitrogen, at 0° C., to a solution of compound of example (1) (300 g, 1.14 mol) and $NaBH_4$ (75 g, 1.97 mol) in dry THF (2.25 L). The temperature of the reaction mixture was slowly raised to 55° C. and stirred for 1.5 h. Ice cold water (100 mL) was slowly added followed by acidification with conc. HCl (375 mL). The reaction mixture was stirred for 1 h. at 50-55° C. It was cooled to 30° C. and basified using 50% aqueous NaOH solution to pH 11-12. Hydrogen peroxide (30%, 225 mL) was added over 0.5 h. The reaction mixture was stirred at 55-60° C. for 1.5 h. It was cooled to 30° C. and sufficient water was added to dissolve the precipitated salts. The organic layer was separated and the aqueous portion extracted with ethyl acetate (2×1 L). The organic extracts were dried (anhydrous $Na_2SO_4$) and concentrated. The crude viscous brown oil obtained was treated with 4N HCl (1.2 L) and extracted with ethyl acetate (2×500 mL). The aqueous portion was cooled, basified with 50% aqueous sodium hydroxide solution and extracted using ethyl acetate (2×1 L). The organic extract was dried (anhydrous $Na_2SO_4$) and concentrated to give the compound, (±)-trans-1-methyl-4-(2,4,6-trimethoxy-phenyl)-piperidin-3-ol Yield: 210 g (65.6%); mp: 96-97° C.; IR (KBr): 3582, 3374, 3017 $cm^{-1}$;
$^1H$ NMR ($CDCl_3$, 300 MHz): δ 6.15 (s, 2H), 4.40 (m, 1H), 3.79 (s, 3H), 3.74 (s, 6H), 3.20 (dd, 1H), 3.00 (m, 1H), 2.80 (m, 1H), 2.40 (m, 1H), 2.37 (s, 3H), 2.00 (m, 1H), 1.90 (t, 1H), 1.52 (m, 1H); MS (CI): m/z 282 (M+1).

Example 3

Preparation of (±)-trans-Acetic acid-1-methyl-3-(2,4,6-tri ethoxyphenyl)-pyrrolidin-2-yl methyl ester Methanesulfonyl chloride (30.27 mL, 44.8 g, 0.4 mol) was added drop wise to a cooled and stirred solution of compound of example (2) (100 g, 0.35 mol) and triethylamine (71.88 g, 0.7 mol) in dry THF (1.0 L). The reaction mixture was further stirred for 45 min. at 0° C. The precipitate of triethylamine HCl was filtered and washed with dry THF (2×100 mL). The filtrate was added dropwise to a refluxing suspension of sodium acetate (115 g, 1.40 mol) in 2-propanol (1.0 L). The reaction mixture was refluxed for a further 15 min., diluted with EtOAc (1.0 L) and salts were filtered. The mixture of salts was washed with EtOAc (2×100 mL). The combined filtrate was concentrated to give a gum. Water (50 mL) was added to the gum with stirring to obtain a solid which was filtered and dried to yield the compound, (±)-trans-acetic acid 1-methyl-3-(2,4,6-trimethoxy-phenyl)-pyrrolidin-2-yl methyl ester.

Yield: 90 g (81%); mp: 74-77° C.; $^1H$ NMR ($CDCl_3$, 300 MHz): δ 6.13 (s, 2H), 4.00 (m, 2H), 3.81 (m, 1H), 3.79 (s, 3H), 3.76 (s, 6H), 3.20 (m, 1H), 2.75 (m, 1H), 2.69 (m, 1H), 2.47 (s, 3H), 2.00 (m, 2H), 1.99 (s, 3H).

Example 4

Preparation of (±)-trans-[1-Methyl-3-(2,4,6-trimethoxyphenyl)-pyrrolidin-2-yl]-methanol A 10% aqueous NaOH solution (596 mL) was added to a solution of the compound of example (3) (241 g, 0.75 mol) in methanol (596 mL). The reaction mixture was stirred at 50° C. for 45 min. It was concentrated to a gum and then poured into ice-cold water (2 L). The resulting solid was filtered to obtain the compound, (±)-trans-[1-methyl-3-(2,4,6-trimethoxy-phenyl)-pyrrolidin-2-yl]-methanol.

Yield: 198 g (94%); mp: 82-85° C.; IR (KBr): 3421, 3009, 1607 $cm^{-1}$;
$^1H$ NMR ($CDCl_3$, 300 MHz): δ 6.15 (s, 2H), 3.92 (m, 1H), 3.80 (s, 9H), 3.60 (dd, 1H), 3.45 (d, 1H), 3.20 (m, 1H), 2.78 (m, 1H), 2.50 (m, 1H), 2.42 (s, 3H), 2.00 (m, 1H), 1.92 (m, 1H); MS (ES+): m/z 282 (M+1).

Example 5

Preparation of (−)-trans-[1-Methyl-3-(2,4,6-trimethoxyphenyl)-pyrrolidin-2-yl]-methanol (−)-DBTA (321.7 g, 897.7 mmol) was added to the compound of example (4) (250 g, 889.6 mmol) followed by addition of methanol (1715 mL). The mixture was refluxed for 10 min., stirred slowly at room temperature for 3 h., the crystallised salt was filtered and dried.

Yield: 185 g (30%); mp: 102-105° C.; $[\alpha]_D^{25} = -82.66°$ (c=0.7, methanol).

The salt was stirred with 10% aqueous solution of $Na_2CO_3$ (765 mL) and EtOAc (200×3 mL) to obtain the free base in the EtOAc layer. The EtOAc layer was concentrated to obtain the compound, (−)-trans-[1-methyl-3-(2,4,6-trimethoxy-phenyl)-pyrrolidin-2-yl]-methanol.

Yield: 80 g (98.3%); $[\alpha]_D^{25} = -20.0°$ (c=0.7, methanol);
$^1$H NMR ($CDCl_3$, 300 MHz): δ 6.13 (s, 2H), 3.90 (m, 1H), 3.79 (s, 9H), 3.57 (dd, 1H), 3.38 (d, 1H), 3.13 (m, 1H), 2.69 (m, 1H), 2.47 (m, 1H), 2.34 (s, 3H), 2.00 (m, 1H), 1.93 (m, 1H).

This compound was subjected to chiral HPLC. Chiral HPLC was done using column Chiralcel OD-H (250×4.6 mm) and solvent system hexane:ethanol (92:08) with TFA (0.4%). The results are recorded at 264 nm with solvent flow rate of 1 mL/min. As depicted in FIG. 1, the chiral HPLC showed 100% e.e of the compound, (−)-trans-[1-Methyl-3-(2,4,6-trimethoxy-phenyl)-pyrrolidin-2-yl]-methanol.

Example 6

Preparation of (−)-trans-Acetic acid-3-(3-acetyl-2-hydroxy-4,6-dimethoxy phenyl)-1-methyl-pyrrolidin-2-yl methyl ester $BF_3$-etherate (25.2 g, 178 mmol) was added dropwise, with stirring, at 0° C., under $N_2$ atmosphere to a solution of the compound of example (5) (10 g, 35.58 mmol) in acetic anhydride (19.48 mL, 176 mmol). The reaction mixture was stirred at room temperature for 2 h. It was poured over crushed ice (1 kg), basified using a saturated aqueous $Na_2CO_3$ solution and extracted using EtOAc (3×200 mL). The organic extract was washed with brine, dried (anhydrous $Na_2SO_4$) and concentrated to obtain the compound, (−)-trans-acetic acid 3-(3-acetyl-2-hydroxy-4,6-dimethoxy-phenyl)-1-methyl-pyrrolidin-2-yl methyl ester.

Yield: 10 g (83%); $^1$H NMR ($CDCl_3$, 300 MHz): δ 14.20 (s, 1H), 5.96 (s, 1H), 4.10 (d, 2H), 3.90 (s, 3H), 3.89 (s, 3H), 3.85 (m, 1H), 3.26 (m, 1H), 2.82 (m, 1H), 2.74 (m, 1H), 2.66 (s, 3H), 2.52 (s, 3H), 2.21 (m, 2H), 2.10 (s, 3H).

Example 7

Preparation of (−)-trans-1-[2-Hydroxy-3-(2-hydroxymethyl-1-methylpyrrolidin-3-yl)-4,6-dimethoxyphenyl]-ethanone To a solution of the compound of example (6) (10 g, 28.4 mmol) in methanol (25 mL) was added with stirring, at room temperature, a 10% aqueous NaOH (25 mL) solution. The temperature of the reaction mixture was raised to 50° C. for 45 min. It was cooled to room temperature, acidified using conc. HCl and concentrated to remove methanol. It was basified using a saturated aqueous $Na_2CO_3$ solution. The compound, (−)-trans-1-[2-hydroxy-3-(2-hydroxymethyl-1-methyl-pyrrolidin-3-yl)-4,6-dimethoxy-phenyl)-ethanone, was filtered, washed with water and dried.

Yield: 7.14 g (82%); IR (KBr): 3400, 3121, 3001, 1629, 1590 $cm^{-1}$;
$^1$H NMR ($CDCl_3$, 300 MHz): δ 5.96 (s, 1H), 3.93 (m, 1H), 3.90 (s 3H), 3.88 (s, 3H), 3.59 (dd, 1H), 3.37 (d, 1H), 3.13 (m, 1H), 2.75 (m, 1H), 2.61 (s, 3H), 2.59 (m, 1H), 2.37 (s, 3H), 2.00 (m, 2H); MS (ES+): m/z 310 (M+1).

Example 8

Preparation of (+)-trans-2-(2-Chlorophenyl)-8-(2-hydroxymethyl-1-methylpyrrolidin-3-yl)-5,7-dimethoxy-chromen-4-one Sodium hydride (50%, 0.54 g, 11.25 mmol) was added in portions to a solution of the compound of example (7) (0.7 g., 2.2 mmol) in dry DMF (15 mL) at 0° C., under nitrogen atmosphere and with stirring. After 10 min., methyl 2-chlorobenzoate (1.15 g., 6.75 mmol) was added. The reaction mixture was stirred at 25° C. for 2 h. Methanol was added carefully below 20° C. The reaction mixture was poured over crushed ice (300 g), acidified with 1:1 HCl (pH 2) and extracted using EtOAc (2×100 mL). The aqueous layer was basified using a saturated $Na_2CO_3$ (pH 10) and extracted using $CHCl_3$ (3×200 mL). The organic layer was dried (anhydrous $Na_2SO_4$) and concentrated. To the residue, conc. HCl (25 mL) was added stirred at room temperature for 2 h. The reaction mixture was poured over crushed ice (300 g) and made basic using a saturated aqueous $Na_2CO_3$ solution. The mixture was extracted using $CHCl_3$ (3×200 mL). The organic extract was washed with water, dried (anhydrous $Na_2SO_4$) and concentrated to obtain the compound, (+)-trans-2-(2-chloro-phenyl)-8-(2-hydroxymethyl-1-methyl-pyrrolidin-3-yl)-5,7-dimethoxy-chromen-4-one.

Yield: 0.67 g (64%); mp: 91-93° C.; $[\alpha]_D^{25} = +5.8°$ (c=0.7, methanol);
IR (KBr): 3431, 1648, 1598, 1571 $cm^{-1}$; $^1$H NMR ($CDCl_3$, 300 MHz): δ 7.70 (dd, 1H), 7.52 (m, 1H), 7.45 (m, 2H), 6.50 (s, 1H), 6.44 (s, 1H), 4.17 (m, 1H), 4.00 (s, 3H), 3.97 (s, 3H), 3.64 (dd, 1H), 3.40 (d, 1H), 3.15 (m, 1H), 2.74 (d, 1H), 2.52 (m, 1H), 2.32 (s, 3H), 2.00 (m, 2H); MS (ES+): m/z 430 (M+1).

Example 9

Preparation of (+)-trans-2-(2-Chlorophenyl)-5,7-dihydroxy-8-(2-hydroxy methyl-1-methyl-pyrrolidin-3-yl)-chromen-4-one Molten pyridine hydrochloride (4.1 g, 35.6 mmol) was added to the compound of example (8) (0.4 g, 0.9 mmol) and heated at 180° C. for 1.5 h. The reaction mixture was cooled to 25° C., diluted with MeOH (10 mL) and basified using $Na_2CO_3$ to pH 10. The mixture was filtered and the organic layer was concentrated. The residue was suspended in water (5 mL), stirred for 30 min., filtered and dried to obtain the compound, (+)-trans-2-(2-chloro-phenyl)-5,7-dihydroxy-8-(2-hydroxymethyl-1-methyl-pyrrolidin-3-yl)-chromen-4-one.

Yield: 0.25 g (70%); IR (KBr): 3422, 3135, 1664, 1623, 1559 $cm^{-1}$;
$^1$H NMR ($CDCl_3$, 300 MHz): δ 7.56 (d, 1H), 7.36 (m, 3H), 6.36 (s, 1H), 6.20 (s, 1H), 4.02 (m, 1H), 3.70 (m, 2H), 3.15 (m, 2H), 2.88 (m, 1H), 2.58 (s, 3H), 2.35 (m, 1H), 1.88 (m, 1H);

MS (ES+): m/z 402 (M+1); Analysis: $C_{21}H_{20}ClNO_5$ C, 62.24 (62.71); H, 5.07 (4.97); N, 3.60 (3.48); Cl, 9.01 (8.83).

Example 10

Preparation of (+)-trans-2-(2-Chlorophenyl)-5,7-dihydroxy-8-(2-hydroxy methyl-1-methyl-pyrrolidin-3-yl)-chromen-4-one hydrochloride (Compound A)

The compound of example (9) (0.2 g, 0.48 mmol) was suspended in IPA (5 mL) and 3.5% HCl (25 mL) was added. The suspension was heated to get a clear solution. The solution was cooled and solid filtered to obtain the compound, (+)-trans-2-(2-Chlorophenyl)-5,7-dihydroxy-8-(2-hydroxymethyl-1-methyl-pyrrolidin-3-yl)-chromen-4-one hydrochloride or Compound A.

Yield: 0.21 g (97%); mp: 188-192° C.; $[\alpha]_D^{25}=+21.3°$ (c=0.2, methanol);

$^1$H NMR (CD$_3$OD, 300 MHz): δ 7.80 (d, 1H), 7.60 (m, 3H), 6.53 (s, 1H), 6.37 (s, 1H), 4.23 (m, 1H), 3.89 (m, 2H), 3.63 (m, 1H), 3.59 (dd, 1H), 3.38 (m, 1H), 2.90 (s, 3H), 2.45 (m, 1H), 2.35 (m, 1H); MS (ES+): m/z 402 (M+1)(free base).

This compound was subjected to chiral HPLC. Chiral HPLC was done using column Chiralcel OD-H (250×4.6 mm) and solvent system hexane:ethanol (92:08) with TFA (0.4%). The results are recorded at 264 nm with solvent flow rate of 1 mL/min. As depicted in FIG. 3, the chiral HPLC showed 100% e.e of the compound, (+)-trans-2-(2-chlorophenyl)-5,7-dihydroxy-8-(2-hydroxy-methyl-1-methyl-pyrrolidin-3-yl)-chromen-4-one hydrochloride Example 11

In-Vitro MTS Assay

The assay has been carried out according to the method described in Molecular Cancer Therapeutics, 2007, 6(9); the disclosure of which is incorporated by reference for the teaching of the assay.

MTS (Promega, Cat #G1111) is a tetrazolium compound ((3-(4,5-dimethylthiazol-2-yl)-5-(3-carboxymethoxyphenyl)-2-(4-sulphophenyl)-2H-tetrazolium, inner salt; MTS) for use in colorimetric assays for determining the number of viable cells in proliferation, cytotoxicity or chemosensitivity assays. This is used with an electron coupling reagent PMS (Phenazine methosulfate). MTS is bioreduced by cells into a formazan that is soluble in tissue culture medium. The absorbance of the formazan at 490 nm can be measured directly from 96 well assay plates without additional processing. Dehydrogenase enzymes found in metabolically active cells accomplish the conversion of MTS into the aqueous soluble formazan. The quantity of formazan product as measured at 490 nm absorbance is directly proportional to the number of living cells in culture.

Before testing the effect of Compound A on radiosensitivity of FaDu (human head and neck cancer, ATCC, USA) cells, the dose dependent cytotoxicity of Compound A alone was determined using MTS assay. Tumor cells were incubated in the presence of various concentrations of Compound A for 48 h and subjected to MTS assay. The IC$_{30}$, IC$_{50}$ and IC$_{70}$ of Compound A in FaDu cells were found to be 0.7, 1.0 and 2 µM respectively. Radiation alone also caused a dose-dependent reduction in cell survival.

Protocol

The Fa-Du (human head and neck cancer, ATCC, USA) cells were seeded at density of 1500 cells/well in 180 µL of MEM (minimum essential medium) in tissue culture grade 96-well plate and allowed to grow for 24 h in humidified 5% CO$_2$ incubator at 37±1° C.

Three identical groups of cells were made. After a time interval of 24 h after seeding, different wells of the first and second group of cells were irradiated at room temperature at dose of 2, 4, 6, 8 and 10 Gy respectively. The second group was further treated 24 h after irradiation (i.e. on the third day of the experiment) with IC$_{30}$ concentration of Compound A. The third group was treated on the third day of the experiment, with IC$_{30}$ concentration of Compound A alone.

In order to obtain IC$_{30}$ concentration (0.7 µM) of Compound A in any well, 20 µL of a stock solution of concentration 10×IC$_{30}$, (i.e. 7 µM) was added to the well (dissolved first in DMSO and then in cell medium, final DMSO concentration should not exceed 0.5%) and diluted to 200 µL with MEM. The wells were incubated for 48 h and 96 h respectively, in humidified 5% CO$_2$ incubator at 37±1° C. After completion of 48 h and 96 h respectively, the medium was removed from all wells and fresh MEM was added and the plates were incubated further for additional 4-6 days or for total of 8-10 days from the start of the experiment. At the end of the experiment, the medium was removed from all wells and 20 µL of MTS (2 mg/ml in phosphate buffer saline, pH 6-6.5 and filter sterilized) and 1 µL of PMS (3 mM in PBS, pH 7.3 and filter sterilized) was added per well along with the cell medium to adjust the total volume to 200 µL/well. The plate was incubated for 2-4 h in humidified 5% CO$_2$ incubator at 37±1° C. The plate was read at 490 nM on Spectrophotometer (SpectraMax, Molecular Devices, USA), and the percentage cytotoxicity using SoftMax, software for SpectraMax was calculated.

The above experiment was repeated using IC$_{50}$ and IC$_{70}$ concentrations of Compound A.

The enhancement in radiation effects in FaDu cell line as evaluated using the CompuSyn software by Chou and Talalay, described in Pharmacological Reviews, 2006, 58, 621-681, which is incorporated herewith by reference. Combination index (CI) is used to evaluate if a combination is additive, synergistic or antagonistic. CI<1 is synergistic, CI=1 is additive and CI>1 is antagonistic. For example, at a treatment of 48 h with a concentration of IC$_{70}$ of Compound A, the combination was synergistic (CI=0.7) at all the doses of radiation. The combination index in both the cases ie. IC$_{30}$ and IC$_{50}$ of Compound A for 96 h treatment was additive (CI=1) at all doses of radiation. At a treatment of 96 h with a concentration of IC$_{70}$ of Compound A, the combination was synergistic at 2, 4 and 6 Gy (CI<1).

Results are given in Table 1, Table 2 and Table 3.

TABLE 1

Effect of Compound A IC$_{30}$ (48 h and 96 h) alone, radiation alone and the combination on cell survival in FaDu cell line in MTS assay

| Treatment Schedule | | % cytotoxicity | |
|---|---|---|---|
| Radiation (24 h after seeding) | Compound A (24 h after radiation) | 48 h after Compound A treatment | 96 h after Compound A treatment |
| 0 | 0.7 µM Compound A | 8 | 4 |
| 2 Gy | 0 | 17 | 2 |
| 4 Gy | 0 | 26 | 10 |
| 6 Gy | 0 | 35 | 20 |
| 8 Gy | 0 | 55 | 46 |
| 10 Gy | 0 | 59 | 71 |
| 2 Gy | 0.7 µM Compound A | 23 | 15 |
| 4 Gy | 0.7 µM Compound A | 35 | 31 |

TABLE 1-continued

Effect of Compound A IC$_{30}$ (48 h and 96 h) alone, radiation alone and the combination on cell survival in FaDu cell line in MTS assay

| Treatment Schedule | | % cytotoxicity | |
|---|---|---|---|
| Radiation (24 h after seeding) | Compound A (24 h after radiation) | 48 h after Compound A treatment | 96 h after Compound A treatment |
| 6 Gy | 0.7 µM Compound A | 64 | 60 |
| 8 Gy | 0.7 µM Compound A | 79 | 69 |
| 10 Gy | 0.7 µM Compound A | 80 | 85 |

TABLE 2

Effect of Compound A IC$_{50}$ (48 h and 96 h) alone, radiation alone and the combination on cell survival in FaDu cell line in MTS assay

| Treatment Schedule | | % cytotoxicity | |
|---|---|---|---|
| Radiation (24 h after seeding) | Compound A (24 h after radiation) | 48 h after Compound A treatment | 96 h after Compound A treatment |
| 0 | 1 µM Compound A | 20 | 25 |
| 2 Gy | 0 | 17 | 2 |
| 4 Gy | 0 | 26 | 10 |
| 6 Gy | 0 | 35 | 20 |
| 8 Gy | 0 | 55 | 46 |
| 10 Gy | 0 | 59 | 71 |
| 2 Gy | 1 µM Compound A | 35 | 25 |
| 4 Gy | 1 µM Compound A | 50 | 37 |
| 6 Gy | 1 µM Compound A | 73 | 77 |
| 8 Gy | 1 µM Compound A | 85 | 84 |
| 10 Gy | 1 µM Compound A | 86 | 90 |

TABLE 3

Effect of Compound A IC$_{70}$ (48 h and 96 h) alone, radiation alone and the combination on cell survival in FaDu cell line in MTS assay

| Treatment Schedule | | % cytotoxicity | |
|---|---|---|---|
| Radiation (24 h after seeding) | Compound A (24 h after radiation) | 48 h after Compound A treatment | 96 h after Compound A treatment |
| 0 | 2 µM Compound A | 66 | 83 |
| 2 Gy | 0 | 17 | 2 |
| 4 Gy | 0 | 26 | 10 |
| 6 Gy | 0 | 35 | 20 |
| 8 Gy | 0 | 55 | 46 |
| 10 Gy | 0 | 59 | 71 |
| 2 Gy | 2 µM Compound A | 79 | 98 |
| 4 Gy | 2 µM Compound A | 86 | 96 |
| 6 Gy | 2 µM Compound A | 89 | 96 |
| 8 Gy | 2 µM Compound A | 91 | 95 |
| 10 Gy | 2 µM Compound A | 91 | 94 |

Conclusions

The MTS assay showed an enhancement in radiation effects in FaDu cell line which was synergistic at 6, 8 and 10 Gy at an exposure of IC$_{30}$ and IC$_{50}$ of Compound A for 48 h following radiation. Even at clinically relevant doses of 2, 4, and 6 Gy alone, considerable enhancement of radioresponse was observed. Similarly, at a concentration of IC$_{70}$ of Compound A, the combination was synergistic at all the doses of radiation.

The enhancement of radioresponse was also observed at 96 h of Compound A treatment. Even though the combination index in both the cases ie. IC$_{30}$ and IC$_{50}$ of Compound A was additive at all doses, it can be clearly seen that there was enhancement of radioresponse which was very significant at 6 Gy. Similarly, at IC$_{70}$ of Compound A, the combination was synergistic at 2, 4 and 6 Gy.

Example 12

In-Vitro Clonogenic Assay

The assay has been carried out according to the method described in Radiotherapy and Oncology, 2004, 71, 213-221; the disclosure of which is incorporated by reference for the teaching of the assay.

As a result of an increasing interest in chemoradiation in the clinic and the development of new agents with radioenhancing potential, there is a growing need for preclinical research on interactions between radiation and chemotherapeutic agents. The clonogenic assay is generally considered the optimal test system for in vitro radiation studies. Indeed for chemosensitivity testing, the colorimetric assays, such as the tetrazolium (MTT/MTS) and the sulforhodamine B (SRB) assays, have replaced the clonogenic assay. However, for radiosensitivity testing the clonogenic assay is still the gold standard. The colorimetric assays are thought to be inadequate to measure radiation sensitivity, due to the short duration of the assays. After radiation treatment, cells destined to die can still undergo one or more cell divisions. Therefore, it takes a considerable period of time before these irradiated cells express their radiation-induced damage.

Protocol

The Fa-Du cells from exponential phase cultures were harvested by trypsinization, counted and plated at a cell density of 1500 cells/well in six-well plate and four identical groups were made. First group served as control that was untreated. Different wells of the second and third group, 24 h after seeding were irradiated at room temperature at dose of 2, 4, 6, 8 and 10 Gy respectively. The third group was further treated, 24 h after irradiation (i.e. on the third day of the experiment) with IC$_{50}$ concentration of Compound A. The fourth group was treated on the third day of the experiment with IC$_{50}$ concentration of Compound A alone.

After completion of 72 h and 96 h respectively, the medium was changed for all the wells and the plates incubated for a total period of 12-14 days from the first day of the experiment (i.e. the cell seeding day) to allow sufficient time for the cells to form colonies of at least 50 cells. The medium was aspirated and colonies were fixed with methanol and acetic acid mixture in the proportion of 2:1. The fixation procedure was repeated after rinsing with water. The plates were dried and colonies stained with 0.1% crystal violet for 5 min. The wells were finally rinsed with water and dried. The colonies were counted and the results are given in Table 4.

The experiment was initially carried out using 3500 cells/well and treatment with Compound A at a dose of 1 µM was carried out for both 48 h and 96 h, but the number of colonies in the control were too many and hence the colonies could not be counted. However, visual enhancement in radiation response was observed as observed in FIG. 1 and FIG. 2. FIG. 3 and FIG. 4 show the visual enhancement in the radiation response by 1 µM dose of Compound A, in FaDu cell line (Seeding density: 1500 cells/plate).

TABLE 4

Effect of Compound A IC$_{50}$ (72 h and 96 h) alone, radiation alone and the combination on cell survival in FaDu cell line in clonogenic assay (Seeding density: 1500 cells/plate)

| Treatment Schedule | | Number of colonies | |
| --- | --- | --- | --- |
| Radiation (24 h after seeding) | Compound A (24 h after radiation) | 72 h after Compound A treatment | 96 h after Compound A treatment |
| 0 (control) | 0 (control) | 138 | 185 |
| 0 | 1 µM Compound A | 38 | 36 |
| 2 Gy | 0 | 105 | 132 |
| 4 Gy | 0 | 70 | 48 |
| 6 Gy | 0 | 42 | 35 |
| 8 Gy | 0 | 11 | 12 |
| 10 Gy | 0 | 0 | 4 |
| 2 Gy | 1 µM Compound A | 45 | 40 |
| 4 Gy | 1 µM Compound A | 18 | 17 |
| 6 Gy | 1 µM Compound A | 7 | 6 |
| 8 Gy | 1 µM Compound A | 0 | 2 |
| 10 Gy | 1 µM Compound A | 0 | 0 |

Conclusions

Treatment with Compound A at a dose of 1 µM for both 72 h and 96 h enhanced the radiation response of these cells at both 4 and 6 Gy.

Example 13

In-Vivo Studies

The assay can be carried out according to the method described in Clinical Cancer Research, 2003, 9, 6052-6061; the disclosure of which is incorporated by reference for the teaching of the assay.

The in-vivo studies can be carried out by using Xenograft models in Severe combined immune deficiency (SCID) mice strain-CBySmn.CB17-Prkdc$^{scid}$/J, by the method described below. The statistically significant number of mice per group (n=6) is chosen in order to be able to statistically evaluate the study data. Six to eight weeks old SCID mice were used. Head and neck cancer cells are grown in MEM medium containing 10% fetal calf serum in 5% CO$_2$ incubator at 37° C. Cells are pelleted by centrifugation at 1000 rpm for 10 minutes. Cells are resuspended in saline to get a count of 30×10$^6$ cells per mL; 0.2 mL of this cell suspension are injected by subcutaneous route in the right flank of SCID mice. Mice are observed every day for palpable tumor mass. Once the tumor reaches a size of 5-10 mm in diameter, animals are randomized into respective groups of drug/radiation treatment and vehicle (saline) treatment. Compound A (i.p.) and radiation are administered as per the schedule with tumor measurement done every day. Body weight for all the groups is recorded for the entire period. Tumor size and other signs of toxicity (external) is recorded every day. Tumor weight (mg) is estimated according to the formula for a prolate ellipsoid: {Length (mm)×[width (mm)$^2$]×0.5}. Tumor growth in compound treated animals is calculated as T/C (Treated/Control)×100% and growth inhibition percent (GI %) was [100−T/C %]

Assignment of Study Groups

Mice are randomized to control and treatment groups when the tumor size attains a size of 5-10 mm in diameter.

Study Design

Fractionated doses of radiation are used. Total radiation dose used is 15 Gy.

Fractionated radiation doses are 3 Gy twice weekly, followed by Compound A 35 mpk (milligram/kg) everyday for 18 days.

Dosing Schedule

All mice are administered the CDK inhibitors by the i.p. route. The control (untreated) animals are injected with saline. Treatment is continued for 18 days as mentioned in study design.

Observation and Measurements

The following parameters are observed
1. Gross animal health—everyday
2. Body weight—everyday
3. Tumor measurement every alternate day.

Tumor weight in milligram is calculated using the formula for a prolate ellipsoid:

Tumor weight (mg)=Length (mm)×[Breadth (mm)$^2$]× 0.5

Treated to control ratio (T/C %) on a given day is calculated using the formula:

$$T/C \% \text{ on Day } X = \frac{\text{Tumor size Compound } A_{Day\ X} - \text{Tumor size Compound } A_{Day\ 0}}{\text{Tumor size control}_{Day\ X} - \text{Tumor size control}_{Day\ 0}} \times 100$$

4. Growth inhibition (GI) is calculated as
   GI on day X=100−T/C % on day X
   CDK inhibitor very active GI %≥75%
   CDK inhibitor moderately active GI %≥50%
   CDK inhibitor weakly active GI %=30-50%
   CDK inhibitor inactive GI %≤30%

Terminal Procedures

At the end of the experiment, animals are euthanized using high dose of pentobarbital sodium (100 mg/kg i.p./i.v.) or exposure to carbon dioxide gas.

Results

The results are as depicted in Table 5. FIG. 5 depicts the average group body weight over the period of drug administration plotted. FIG. 6 depicts the average % tumor weight of Head and Neck carcinoma (FaDu) xenograft over a period of 18 days.

TABLE 5

Average % growth inhibition (% GI) in the various groups with respect to control group

| Groups | Only radiation | Only Compound A | Radiation + Compound A |
| --- | --- | --- | --- |
| % Growth inhibition | 43 | 42 | 75 |

Conclusion

The combination of radiation followed by Compound A showed significant in vivo efficacy in the human FaDu xenograft model than either radiation or Compound A alone.

Example 14

Clinical Protocol

The clinical studies can be carried out by the method described below.

Primary Objective:

To determine the maximum tolerated dose (MTD) and dose limiting toxicity (ies) (DLT/s) of Compound A in combination with radiation in subjects with recurrent and/or locally advanced squamous cell carcinoma of head and neck (SCCHN)

Secondary Objectives:
1. To evaluate safety and tolerability of the combination regimen of Compound A and radiation in the study population;
2. To analyze pharmacokinetics (PK) of Compound A in the study population; and
3. To evaluate efficacy of the combination regimen of Compound A and radiation in the study population.

Study Design:

This is a phase I/II open label study to evaluate safety and efficacy of Compound A in combination with radiation in subjects with recurrent and/or locally advanced squamous cell carcinoma of head and neck. It is expected that approximately 22 to 28 subjects will be enrolled in the study.

In the phase I component, 3 subjects per cohort are treated with Compound A and radiation in a 21-day cycle following which a safety assessment is performed. If the regimen is tolerated in the first cycle, then Compound A dose escalation is performed in the next cohort of 3 subjects.

Compound A dose escalation proceeds as follows:
1) 3 subjects are entered at dose level 1 (100 mg/m²/day as 30 minutes i.v. infusion).
2) If none of the 3 subjects experience DLT during cycle 1, dose escalation is continued as per protocol design.
3) If one of three subjects experiences first cycle DLT, up to three additional subjects are added to this cohort (maximum 6) and if none of these 3 additional subjects experience DLT, dose escalation is allowed.
4) If 2 subjects in the initial or expanded cohort (2 of 6) experience first cycle DLT, this dose is labeled as Maximally Administered Dose (MAD) and the MTD, same as the recommended phase II dose (RPTD) is the previous dose at which ≤⅙ subjects experienced a DLT. In the phase II component, 10 additional subjects are enrolled at the RPTD to evaluate clinical efficacy and to further define the safety profile of the regimen.

The Compound A dose levels for phase I component are shown in the table 6 below:

TABLE 6

| Dose levels of Compound A for phase I component | | |
|---|---|---|
| Level 1 | N/A | 100 mg/m²/day x 5 q 3 weeks |
| Level 2 | 40% (40 mg) | 140 mg/m²/day x 5 q 3 weeks |
| Level 3 | 32% (44.8 mg) | 185 mg/m²/day x 5 q 3 weeks |

There is no intrasubject dose escalation.

The initial dose of Compound A in this study (100 mg/m²/day) is almost half the single agent RPTD of Compound A. The dosing regimen is as used in the phase I study for determination of RPTD.

Study Treatments:

Compound A is administered at dose as described above as an intravenous infusion in 5% dextrose over 30 minutes from day 1 to day 5 in each 21 day cycle. All subjects also receive external beam radiotherapy to involved regions by using standard conventional fractionation i.e. 2 Grays (Gy) per day for 5 days a week for a total radiation dose of 60 Grays (Gy). Total radiation dose for spinal cord is less than 46 Gy. The Compound A and radiotherapy treatment are administered for six weeks i.e. 2 cycles of Compound A and 60 fractions of radiation. One 21-day cycle of the combination regimen comprises of Compound A dosing from days 1 to 5 and radiotherapy (2 Gy per day) on days 1 to 5, 8 to 12 and 15 to 19. Subjects are discontinued in the event of progression of disease (clinical or objective) or unacceptable toxicity.

We claim:

1. A method for the treatment of cancer comprising administering to a subject in need thereof a combination comprising radiation and a CDK inhibitor of formula I or a pharmaceutically acceptable salt or a solvate thereof:

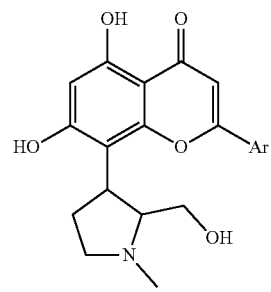

Formula I wherein Ar is phenyl, which is substituted by 1 or 2 different substituents selected from the group consisting of: chlorine, nitro, cyano, $C_1$-$C_4$-alkyl and trifluoromethyl; wherein the cancer is head and neck cancer.

2. The method according to claim 1, wherein the CDK inhibitor is the (+)-trans isomer of the compound of formula I or a pharmaceutically acceptable salt or a solvate thereof, as represented by Formula IA;

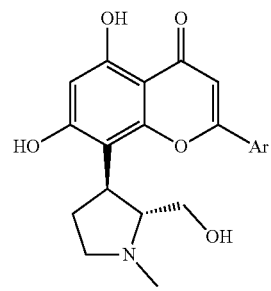

Formula IA wherein Ar is phenyl, which is substituted by 1 or 2 different substituents selected from the group consisting of: chlorine, nitro, cyano, $C_1$-$C_4$-alkyl and trifluoromethyl.

3. The method according to claim 2, wherein the CDK inhibitor of formula I is (+)-trans-2-(2-chloro-phenyl)-5,7-dihydroxy-8-(2-hydroxymethyl-1-methyl-pyrrolidin-3-yl)-chromen-4-one or its pharmaceutically acceptable salt.

4. The method according to claim 1, wherein a therapeutically effective amount of radiation and a therapeutically effective amount of the CDK inhibitor of formula I or a pharmaceutically acceptable salt or a solvate thereof, are administered simultaneously or sequentially to a subject in need thereof.

5. The method according to claim 4, wherein a therapeutically effective amount of radiation and a therapeutically effective amount of the CDK inhibitor of formula I or a pharmaceutically acceptable salt or solvate thereof, are administered sequentially to a subject in need thereof.

6. The method according to claim 5, wherein a therapeutically effective amount of radiation is administered prior to a therapeutically effective amount of the CDK inhibitor of formula I or a pharmaceutically acceptable salt or solvate thereof to a subject in need thereof.

* * * * *